(12) United States Patent
Burghardt et al.

(10) Patent No.: US 9,611,204 B2
(45) Date of Patent: *Apr. 4, 2017

(54) METHOD OF REGULATING THE WATER CONTENT IN A CONTINUOUS METHOD FOR PRODUCING METHACROLEIN

(71) Applicant: EVONIK ROEHM GMBH, Darmstadt (DE)

(72) Inventors: Rudolf Burghardt, Darmstadt (DE); Frederik Gluth, Duesseldorf (DE); Gerhard Koelbl, Gernsheim (DE); Steffen Krill, Muehltal (DE); Torsten Balduf, Pfungstadt (DE)

(73) Assignee: EVONIK RÖHM GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/904,777

(22) PCT Filed: Jul. 15, 2014

(86) PCT No.: PCT/EP2014/065065
§ 371 (c)(1),
(2) Date: Jan. 13, 2016

(87) PCT Pub. No.: WO2015/010942
PCT Pub. Date: Jan. 29, 2015

(65) Prior Publication Data
US 2016/0159719 A1    Jun. 9, 2016

(30) Foreign Application Priority Data
Jul. 24, 2013   (EP) .................................... 13177889

(51) Int. Cl.
C07C 45/75 (2006.01)
C07C 45/82 (2006.01)
C07C 45/78 (2006.01)

(52) U.S. Cl.
CPC ............ *C07C 45/75* (2013.01); *C07C 45/786* (2013.01); *C07C 45/82* (2013.01)

(58) Field of Classification Search
CPC ................................ C07C 45/75; C07C 45/82
USPC .......................................................... 568/461
See application file for complete search history.

(56) References Cited

U.S. PATENT DOCUMENTS

| 4,316,878 A * | 2/1982 | Akune .................... F23G 5/165 423/235 |
| 4,408,079 A | 10/1983 | Merger et al. |
| 4,496,770 A * | 1/1985 | Duembgen ............. C07C 45/75 568/463 |
| 2016/0031786 A1 | 2/2016 | Balduf et al. |
| 2016/0068464 A1 | 3/2016 | Krill et al. |

OTHER PUBLICATIONS

K. Jian, et al., "Asymmetric PVDF hollow-fiber membranes for organic/water pervaporation separations," Journal of Membrane Science, vol. 135, No. 1, XP004096369, Nov. 12, 1997, pp. 41-53.
International Search Report issued Nov. 10, 2014 in PCT/EP2014/065065 filed Jul. 15, 2014.
U.S. Appl. No. 14/904,898, filed Jan. 13, 2016, Krill, et al.
U.S. Appl. No. 14/916,440, filed Mar. 3, 2016, Krill, et al.
U.S. Appl. No. 15/037,171, filed May 17, 2016, Burghardt, et al.
U.S. Appl. No. 15/030,775, filed Apr. 20, 2016, Krill, et al.

* cited by examiner

*Primary Examiner* — Sikarl Witherspoon
(74) *Attorney, Agent, or Firm* — Oblon, McClelland, Maier & Neustadt, L.L.P.

(57) ABSTRACT

The present invention concerns regulating the water content in a process for production of methacrolein. Methacrolein is used in chemical synthesis particularly as an intermediate for production of methacrylic acid, methyl methacrylate or else of active, aroma or flavor chemicals. The present invention is particularly concerned with regulating the water content in a process for production of methacrolein from formaldehyde and propionaldehyde via a Mannich condensation.

19 Claims, 2 Drawing Sheets

Figure 1:
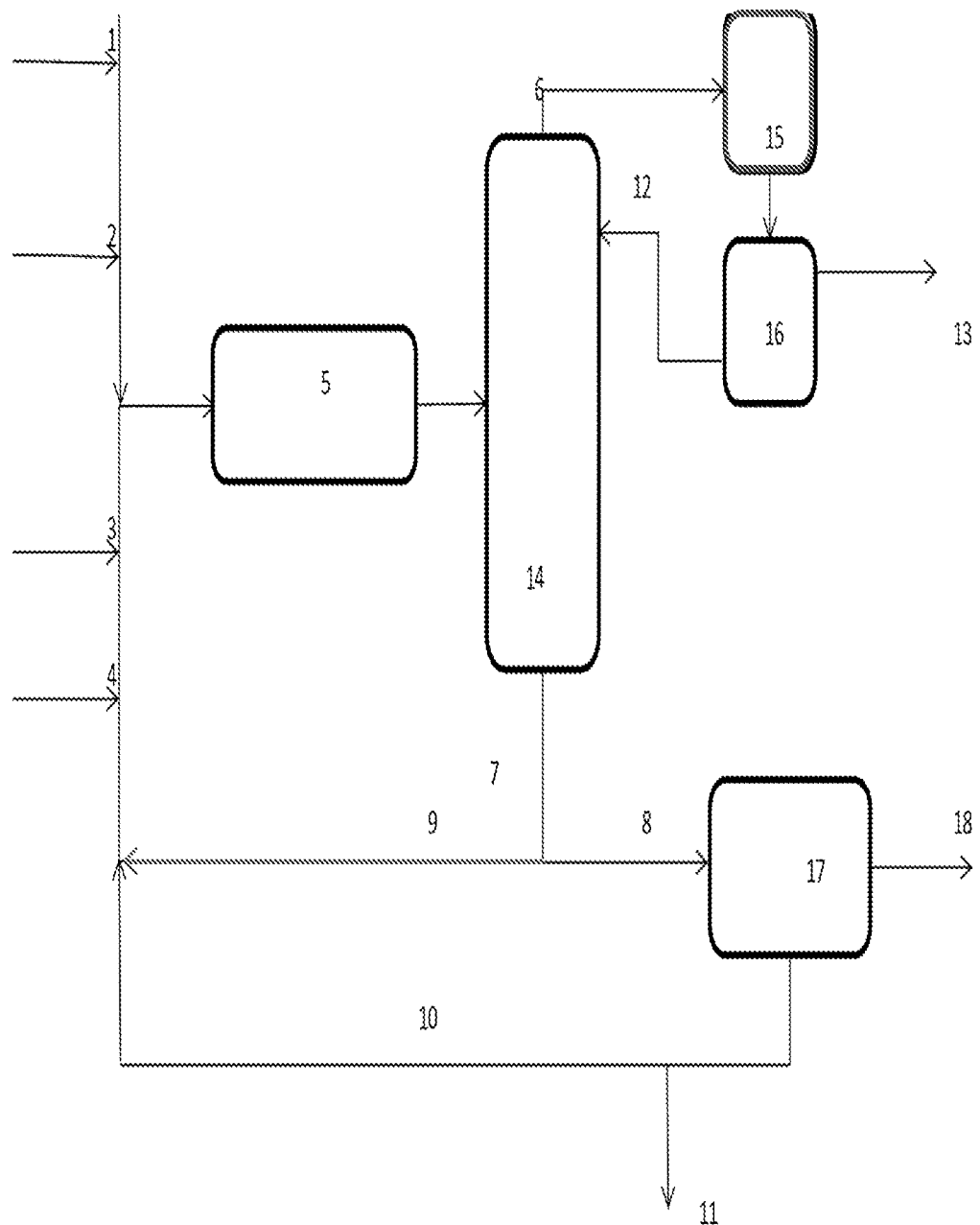

METHOD OF REGULATING THE WATER CONTENT IN A CONTINUOUS METHOD FOR PRODUCING METHACROLEIN

CROSS-REFERENCE TO RELATED APPLICATIONS

This application is a National Stage of PCT/EP2014/065065, which was filed on Jul. 15, 2014. This application is based upon and claims the benefit of priority to European Application No. 13177889.6, which was filed on Jul. 24, 2013.

The present invention concerns regulating the water content in a process for production of methacrolein. Methacrolein is used in chemical synthesis particularly as an intermediate for production of methacrylic acid, methyl methacrylate or else of active, aroma or flavour chemicals. The present invention is particularly concerned with regulating the water content in a process for production of methacrolein from formaldehyde and propionaldehyde via a Mannich condensation.

There is considerable interest in very simple, economical and environmentally benign processes for producing methacrolein.

PRIOR ART

Various amine-catalytic processes are known to generate amine-containing water of reaction, in particular processes for producing methacrolein. One prominent large-scale industrial process for producing methacrolein proceeds from propanal and formaldehyde and involves a Mannich reaction. Such a process for producing methacrolein is described inter alia in the printed publications U.S. Pat. No. 7,141,702, U.S. Pat. No. 4,408,079, JP 3069420, JP 4173757, EP 0 317 909 and U.S. Pat. No. 2,848,499.

As will be appreciated, there is particular interest in performing this reaction in a continuous manner. This generates amine-containing water as by-product of the Mannich reaction or of an aldol-like addition reaction. This water is the reaction medium and solvent for the reactants and the catalyst solution, and is needed particularly for moderating the heat of reaction and the reaction regime. On the other hand, a process of this type is designed to recirculate the water, which contains the catalyst, for example. However, a disadvantage with this is that over time the water builds up in the reaction circuit and has to be removed. Following the substantial removal of reaction product, i.e. methacrolein, the water is sent for disposal together with active and inactive constituents of the catalyst.

It must further be borne in mind that water can also be imported into the reaction with the starting materials and also optionally with the catalyst components and co-affect the level of water in the reaction.

Thus, the formalin used will import appreciable amounts of water into the system; depending on the choice of strength/concentration for the formalin (commercially available formalin concentrations between 30-60 wt % of formaldehyde in water are typically used in production), the result is thus per se a base load of water which, after the product of value, methacrolein, has been separated off has to be treated together with the water formed during the reaction. It must further be borne in mind as regards the water level in the reaction and the work-up that secondary reactions also generate water. This holds not only for the secondary reactions of the propanal but also for the secondary reactions of the catalytically active amines. The catalytically active amines under the reaction conditions undergo an Eschweiler-Clarke or a Leukart Wallach-like reaction to form more highly alkylated derivatives, some of which are not catalytically active. For instance, dimethylamine will react with one formaldehyde equivalent to form trimethylamine and water.

On the other hand, a process of this type is designed to recirculate the water, which contains the catalyst, for example. However, a disadvantage with this is that over time the water builds up in the reaction circuit and has to be removed. If, by contrast, recycling is eschewed, new catalyst has to be added at the start of the reaction. This makes the process less economical and the wastewaters ecologically concerning. Furthermore, the aqueous phase will also contain certain amounts of unremoved methacrolein, which is thus exported from the system and thereby diminishes the overall yield of the process. Recycling the aqueous phase is described for example in JP 4173757A (JP 19900300135).

DE 32 13 681 proposes several alternatives in this regard. When catalyst levels are low in the aqueous phase or, to be more precise, the distillation bottom product, which in addition to the aqueous phase and the catalyst further contains high-boiling by-products and residual monomers and methacrolein, it is proposed that said bottom product be disposed of. When concentrations are higher, the proposal is to subject the bottom product to a further, very elaborate distillation in order to reduce the water level. The remainder would then be returned into the reaction space. However, this procedure is unfavourable not just in energy terms but also because such a second distillation would at the same time involve a yield-lowering discard of methacrolein, since it would be co-distilled off because of its lower boiling point.

In a third alternative of DE 32 13 681, the bottom product is divided and one portion is returned into the reaction space such that the water content is increased and can be influenced. The other portion of the bottom product—and hence of the aqueous phase—is discarded. However, this procedure has the disadvantage that the discarded fraction in addition to product also contains catalyst quantities which have to be resupplied to the system afresh as replenishment. This not only reduces yield but also increases the catalyst consumption.

PROBLEM

The problem addressed by the present invention in view of the prior art was accordingly that of regulating the water content in a continuous reaction where water of reaction is formed. The problem addressed by the present invention was more particularly that of regulating the water content in a continuous Mannich reaction.

The problem addressed by the present invention was more particularly that of regulating the water content in a continuous Mannich reaction for production of methacrolein wherein a distillation bottom product returned into the reaction space is merely deprived of water and small amounts of other constituents.

The problem addressed by the present invention was further additionally that of removing the water such that it is subsequently available for a biological work-up and another exported phase, which contains high boilers and has a lower water content, is obtained for incineration in a thermal oxidizer.

The process should further be implementable with relatively simple and inexpensive modifications to existing plant. The modifications should accordingly be associated with low capital costs. Moreover, the post-modification plant should be simple and inexpensive to service and maintain. The problem addressed by the present invention is more particularly that of providing a process which, as compared with the prior art, has reduced energy requirements and achieves lower catalyst effluence.

Further problems addressed but not explicitly defined will become apparent from the overall context of the description which follows and the claims.

SOLUTION

These problems are solved by a novel type of process, which is suitable for continuous operation of a Mannich reaction. This process is characterized in that an aqueous phase which contains at least one amine catalyst is separated by at least one membrane separation stage into a stream consisting predominantly of water and a stream of reduced water content.

The reaction product of the reaction can be at least partially separated off beforehand in a column, for example. In this case, the water-containing effluent is withdrawn underneath the feedpoint for this column, for example, and is subsequently separated by at least one membrane separation stage.

It is particularly preferable for the water-containing effluent of the column to be divided after withdrawal. In this case, a first portion of this withdrawal is directed onto the membrane separation stage and the other portion is directed back into the reaction space. This makes it possible to maintain a constant water content in the reaction space. It is particularly preferable to maintain a constant flow for the stream directed back into the reaction space. Correspondingly, the portion/stream directed onto the membrane stage can vary with regard to its volume according to the bottom product quantity, in particular the water quantity in the column.

As an alternative to this preferred embodiment, however, other embodiments are also possible. For instance, the reaction product can also be separated in a phase separator from the aqueous phase which contains at least one amine catalyst. In such a case, this aqueous phase is wholly or partly directed to the membrane separation stage and the reaction product is transferred into, for example, a distillation column. The bottom product of this column can in turn then be directed back into the phase separator, onto the membrane separation stage, back into the reaction space or directly into a, for example thermal, disposal unit.

The membranes of the membrane separation stage are preferably selected such that the stream which consists predominantly of water is the permeate of the membrane separation stage and the stream of reduced water content is the retentate of the membrane separation stage. However, it is also possible to employ membranes where the stream of reduced water content is the permeate and the stream which consists predominantly of water is the retentate.

This first preferred embodiment, where the stream which consists predominantly of water is the permeate of the membrane separation stage and the stream of reduced water content is the retentate of the membrane separation stage, will now be described by way of example to facilitate comprehension of the invention. However, it is explicitly noted that the remainder of the description at all times, unless there is an explicit statement to the contrary, also comprehends the less preferred, converse embodiment wherein the stream of reduced water content is the permeate and the stream which consists predominantly of water is the retentate.

Preferably, the upstream Mannich reaction is a reaction of an aldehyde having 2 to 6 carbon atoms with formaldehyde to form an unsaturated aldehyde in a reaction space. It is particularly preferable for it to be a Mannich reaction where propanal is reacted with formaldehyde to form methacrolein.

In particular, the reaction is carried out in the presence of 0.1 to 20 mol % of an organic base, preferably a secondary amine, and 0.1 to 20 mol % of an acid, preferably an organic acid, each based on the aldehyde of 2 to 6 carbon atoms, at a temperature of 100 to 300° C. and a pressure of 5 to 100 bar. The pressure and temperature settings are generally such that the reaction always stays below the boiling point of the reaction mixture, i.e. that the reaction takes place in the liquid phase.

The processes which are suitable for production of methacrolein and based on a Mannich reaction are known to a person skilled in the art and are the subject of corresponding review articles, for example in Ullmann's Encyclopedia of Industrial Chemistry 2012, Wiley-VCH Verlag GmbH & Co. KGaA, Weinheim, Acrolein and Methacrolein, DOI: 10.1002/14356007.a01_149.pub2. More particularly, the process which, according to the invention, is carried out with particular preference before the introduction of the amine-containing water of reaction relates to a continuous Mannich reaction as disclosed in the European patent application having application number 13002076.1. To clarify that a preliminary stage of this type is preferred according to the present invention, the disclosure of this application as regards methacrolein synthesis is hereby incorporated herein by reference.

The acids are generally inorganic acids or organic mono-, di- or polycarboxylic acids, preferably monocarboxylic acids, in particular aliphatic monocarboxylic acids. It is particularly preferable for the reaction between propanal and formaldehyde to employ at least one organic acid, more preferably acetic acid. The proportion of acid is between 0.1 and 20, advantageously from 0.5 to 10, preferably 1 to 5 mol %, based on propanal.

The organic bases are preferably amines, more preferably secondary amines. Useful amines include, for example, dimethylamine, diethylamine, methylethylamine, methylpropylamine, dipropylamine, dibutylamine, diisopropylamine, diisobutylamine, methylisopropylamine, methylisobutylamine, methylsecbutylamine, methyl(2-methylpentyl)amine, methyl(2-ethylhexyl)amine, pyrrolidine, piperidine, morpholine, n-methylpiperazine, n-hydroxyethylpiperazine, piperazine, hexamethyleneimine, diethanolamine, methylethanolamine, methylcyclohexylamine, methylcyclopentylamine, dicyclohexylamine or corresponding mixtures. The proportion of organic base is between 0.1 and 20, advantageously from 0.5 to 10, preferably 1 to 5 mol %, based on propanal.

The ratio of equivalents of amine to acid is preferably so chosen that a pH of 2.5 to 9 results in the reaction mixture before the reaction.

The amine-containing water of reaction, in addition to the recited components and by-products, may additionally contain unconverted reactants or their descendant products such as paraformaldehyde, or organic solvents such as, for example, propanol, dioxane, tetrahydrofuran, methoxyethanol. More particularly, by-products of the catalyst system, for example tertiary amines or salts thereof, may also be contained.

The product, e.g. methacrolein, is preferably separated off in such a process via a distillation column, as described. The feedpoint of the column is situated in its lower half. The bottom product of this column consists predominantly of the reaction's water of reaction. This additionally contains the catalyst components, for example the organic acid and the secondary amine, or the salt formed from these, and also by-products of the reaction. This aqueous catalyst solution can be withdrawn below the feedpoint, in particular at the base of the column. The water of reaction is composed of the water added as catalyst solution, the water formed in the course of the reaction and optionally the water of the formaldehyde solution.

In an aldol condensation or a Mannich reaction, for example the formation of methacrolein from propanal and formaldehyde, the reaction mixture is preferably directed into a column and stripped therein with steam. The product leaves at the top of the column together with water. The mixture is condensed and separated via a phase separation vessel into an upper phase and a lower phase. The upper phase contains the product, for example methacrolein. The lower phase consists mainly of water. This water may preferably be returned at least partly, preferably wholly, back into the column to remove the product still dissolved in this water.

The water of reaction from the preparation of methacrolein from propanal and formaldehyde is composed of the water added as catalyst solution, the water formed in the course of the reaction and optionally the water from the formaldehyde solution. Further, but minor sources of water are constituents of technical-grade reactants such as propional and water formed in various secondary reactions of the catalyst components with reactants, by-products and reaction products, and also water of reaction from all these components which are formed under the reaction conditions. This amine-containing water of reaction may additionally contain unconverted reactants or their descendant products as well as the recited components and by-products. More particularly, there are the catalyst components, such as a secondary amine and an organic acid, and also the salt formed therefrom. By-products of these catalysts are of particular interest for disposal. Especially more highly alkylated amines, in particular trimethylamine when dimethylamine was used as the original catalytic amine, must be mentioned here by way of example. Small amounts of reactants or product can also be present in the amine-containing water of reaction. Examples thereof are methacrolein, formaldehyde, paraformaldehyde and propanal. By-products of the reaction which are similarly present in the amine-containing water of reaction include, for example, dimers, oligomers or polymers of methacrolein. Depending on the processing procedure, further auxiliary materials, such as organic solvents, e.g. methanol, formic acid, propanol, dioxane, tetrahydrofuran or methoxyethanol, can further be present, as can be further materials included or formed in the reaction matrix.

In one special, preferred embodiment of the invention, the stream which consists predominantly of water, preferably the permeate of the first membrane separation stage, is separated by a second membrane separation stage into a second stream consisting predominantly of water, preferably into a second water-containing permeate, and a second stream of reduced water content, preferably a second retentate. This second permeate has a very high water content and a very low proportion of catalyst components, product, reactants and by-products. It is accordingly possible in most instances to send this permeate for biological disposal. Such a disposal would not be possible with the wastewater of a similar plant which is not in accordance with the present invention. It would require an additional distilling step to recover less contaminated water or alternatively the wastewater would have to be sent for thermal disposal, for example in a thermal oxidizer.

Even the first permeate of the first membrane separation stage from the process according to the present invention may already be amenable to a biological work-up. This depends on the method of operating the plant and on the resultant contamination of the permeate with the materials mentioned. In any event, such a permeate is less contaminated with these materials than a column bottom product exported from the plant. Hence even a more contaminated permeate would be simpler to clean up by distillation.

The process of the present invention further has—irrespective of the embodiment with one or two membrane separation stages—the immense advantage over the prior art that catalyst components dissolved in the bottom product of the column in this way largely remain within the plant. This is highly advantageous over a mere withdrawal of the bottom product for the purpose of reducing the water content. The same also holds for reaction product dissolved in the bottom product. Since this reaction product is not co-exported in the membrane separation stages, it is even the case that the overall yield of the process is increased by the inventive method.

This method/process of the present invention may utilize, for example, nanofiltration or reverse-osmosis membranes that are suitable for removing water from a mixture. Membranes known for this are membranes from the field of water treatment and/or water desalination which are otherwise used for example for producing potable water or boiler feed water in power stations. These are preferably membranes comprising a separation-active layer of polyamide, cellulose acetate or ployether sulphone, particularly preferably of a polyamide. Dow's Filmtec SW30HR membrane is a highly suitable example thereof.

The membranes are generally in the form of spiral-wound elements. The exact construction of such membranes can be reviewed for example in Th. Melin, R. Rautenbach *Membranverfahren—Grundlagen der Modul—und Anlagenauslegung,* 3rd edition, Springer Verlag, Berlin, pp. 173-175.

According to the present invention, the membrane separation stage preferably has a local temperature at the membrane between 10 and 70° C., preferably between 30 and 40° C. It is similarly preferable for the transmembrane pressure to be between 20 and 100 bar, preferably between 50 and 90 bar and more preferably between 70 and 90 bar. The exact plant technology for including the membrane stages in such a production plant is known to a person skilled in the art and can be reviewed for example in Th. Melin, R. Rautenbach *Membranverfahren—Grundlagen der Modul—und Anlagenauslegung,* 3rd edition, Springer Verlag, Berlin, pp. 205-226 and 245-308.

The first retentate recovered at the first or only membrane separation stage is preferably wholly or partly returned into the reaction space. In part is to be understood as meaning in this case that a portion of the retentate is exported to remove by-products which would otherwise build up in the plant. This can be done in a continuous manner. Optionally, this exportation is done batchwise. An exportation can thus be done at regular intervals, for example. It is particularly preferable to use in-line probes to determine the content level of such by-products. In this case, the exporting can be done on exceedance of a predetermined limit. Depending on the nature of the by-product, these probes may concern a pH determination, an IR or RI probe, a viscosity determination or conductivity measurement. It is also possible to obtain corresponding data from the temperature probes in the distillation column. However, it is also simply possible to measure the exported water quantity of the permeate at a point downstream of the membrane separation stages. Moreover, this exported water can be measured to determine the concentration of co-exported water. It is also possible to determine the amount of exported catalyst components, or their descendant products, in the retentate.

This means that the by-products which form are very simple to remove from the reaction mixtures, so the process can be performed with a high overall yield without any need for elaborate purifying steps.

In addition, the water content and/or catalyst content in the production plant can be determined. This may be done for example in the line for returning the retentate into the reaction space. Especially following a withdrawal of retentate for the reasons explained there is a need to make good the catalyst concentration, for example by admixing an organic acid and an amine. If necessary, catalyst can then be introduced into the reaction space on the basis of these measurements.

It is further possible for the exported permeate to remove from the plant more water than is formed in the reaction and/or supplied to the plant by the reactant and catalyst admixture. For this it is preferable for the water content to be determined in the line for returning the retentate, or directly in the reaction space, by means of a suitable probe in an on-line manner. It is particularly preferable to simply determine the amount of water removed by the membrane separation stages. Further water can then be admixed to operate the plant using a constant concentration of water.

Preferably, the water content in the inlet to the reaction space is not greater than 75% of the overall mass.

As explained, a retentate can be sent for incineration, for example in a thermal oxidizer. In particular, the second retentate may be sent either for incineration and/or to the first membrane separation stage and/or to the reaction space. This results in a very efficient removal of water and, in the event of recycling, in only very small amounts of liquid waste that has to be incinerated. Furthermore, this phase fed to the thermal oxidizer has a distinctly lower water content than in the prior art and therefore can be incinerated in a distinctly more energy-saving manner.

The first retentate, by contrast, is preferably either directed back into the reaction space and/or more preferably—as explained—only directed into an incineration if necessary.

In a further embodiment of the invention, the plant can further be engineered such that the aqueous effluent from the bottom part of the distillation column is directed either to the first membrane separation stage and/or proportionally back into the reaction space. This can first be done continuously by simply separating the stream into part-streams. One part-stream may carry precisely the amount of water needed to export via the membrane separation stages that amount of water which was formed in the reaction and was introduced with the starting materials. This part-stream is then exported and directed to the membrane separation stage. The other part-stream is returned into the reactor.

Secondly, the flux can also be controlled according to requirements. It is thus possible, for example, to start up the plant by operating exclusively under recycling into the reaction space and not to direct the bottom product onto the membrane separation stage until a major amount of water has collected in the plant. Moreover, such a changeover, for example in the form of a valve or of a three-way cock, can also be automatically controlled with regard to the water content and/or the by-product concentration via probe-captured data.

One immense advantage of the present invention is that the process can be carried out with relatively simple and inexpensive modifications to existing plant. The modifications are associated with low capital costs. The modified plant is simple and inexpensive to service and maintain. To service it, for example, the stream can be made to bypass the particular membrane separation stage. It is thus possible to clean the particular membrane separation stage, for example with membrane-cleaning agents, while operation is ongoing in the actual production plant.

It is further also possible for example to operate a membrane separation stage with two or more membranes in a parallel arrangement. Such an embodiment of the invention even makes it possible to continue to use the membrane separation stage whilst individual membranes are switched off-line and are cleaned.

LIST OF REFERENCE SIGNS IN THE DRAWINGS

Figure 2:
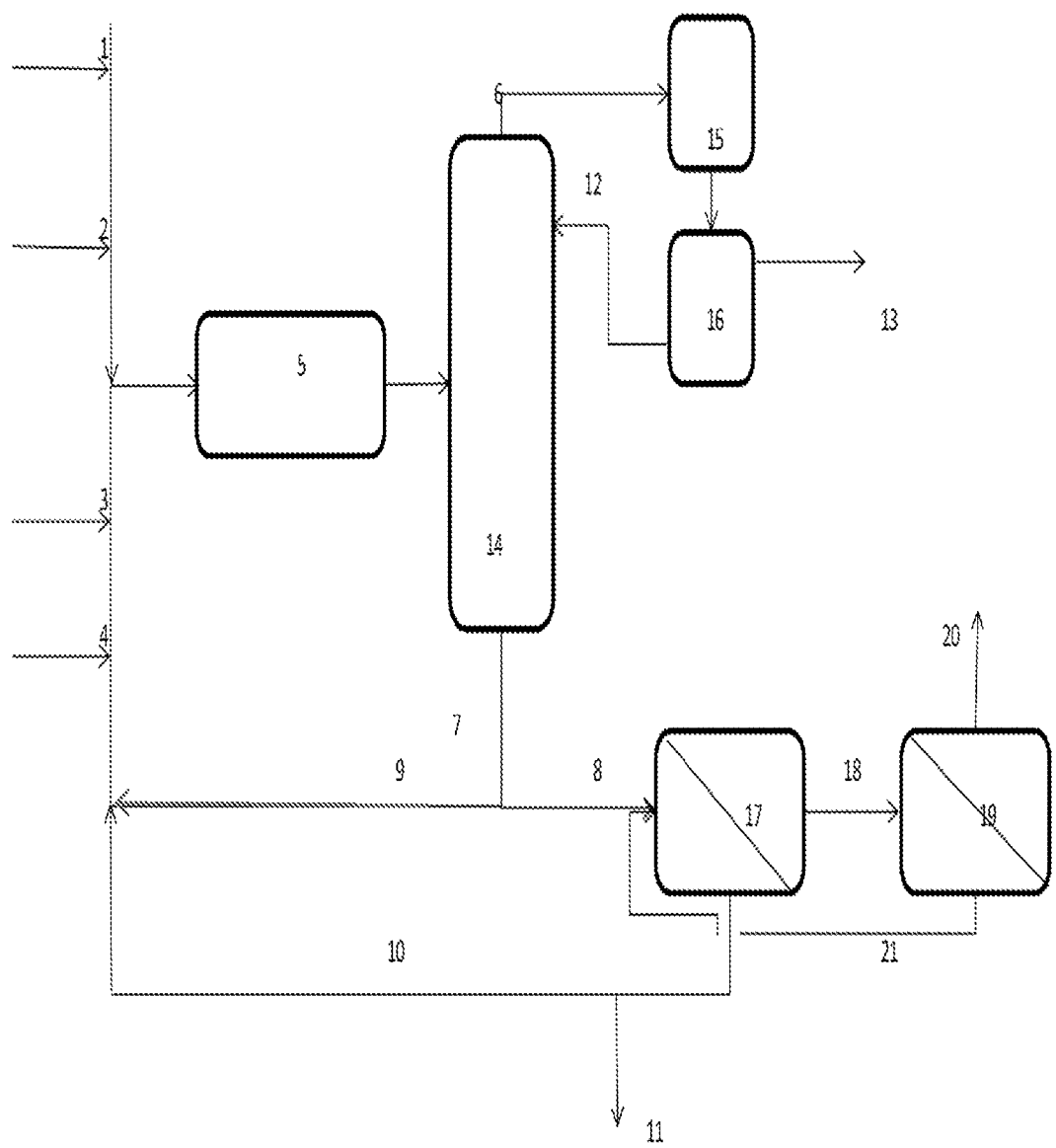

FIG. 1: Embodiment with one membrane stage
1 formalin metering
2 propionaldehyde metering
3 dimethylamine metering
4 acetic acid metering
5 reactor and reaction space
6 head product of column
7 bottom product
8 feed line to membrane separation stage
9 return line for column bottom product to reactor
10 return line for membrane stage retentate to reactor
11 export line for retentate
12 return line for aqueous phase to column
13 methacrolein product
14 distillation column
15 condenser
16 phase separator
17 membrane separation stage
18 permeate
FIG. 2: Embodiment with two membrane separation stages
1 formalin metering
2 propionaldehyde metering
3 dimethylamine metering
4 acetic acid metering
5 reactor and reaction space
6 head product of column
7 bottom product
8 feed line to membrane separation stage
9 return line for column bottom product to reactor
10 return line for membrane stage retentate to reactor
11 export line for retentate
12 return line for aqueous phase to column
13 methacrolein product
14 distillation column
15 condenser
16 phase separator
17 1st membrane separation stage
18 permeate of 1st membrane separation stage to 2nd membrane separation stage
19 2nd membrane separation stage
20 permeate of 2nd membrane separation stage
21 retentate of 2nd membrane separation stage to 1st membrane separation stage

The invention claimed is:

1. A process for continuous operation of a Mannich reaction, the process comprising:
separating an aqueous phase which contains at least one amine catalyst by at least one membrane separation stage into a stream consisting predominantly of water and a stream of reduced water content.

2. The process according to claim 1, wherein the reaction product is at least partially separated off in a column and in that a water-containing effluent is withdrawn underneath the feedpoint for this column and is subsequently separated at least partially by at least one membrane separation stage.

3. The process according to claim 2, wherein the water-containing effluent is divided and one portion is directed onto the membrane separation stage and the other portion is directed back into the reaction space.

4. The process according to claim 1, wherein the stream which consists predominantly of water is the permeate of the membrane separation stage and the stream of reduced water content is the retentate of the membrane separation stage.

5. The process according to claim 1, wherein propanal or another aldehyde comprising 2 to 6 carbon atoms is reacted with formaldehyde in a reaction space to form methacrolein or another unsaturated aldehyde.

6. The process according to claim 5, wherein the reaction is carried out in the presence of 0.1 to 20 mol % of an organic base, optionally a secondary amine, and 0.1 to 20 mol % of an acid, each based on the aldehyde comprising 2 to 6 carbon atoms, at a temperature of 100 to 300° C. and a pressure of 5 to 100 bar.

7. The process according to claim 1, wherein the stream which consists predominantly of water is separated by a second membrane separation stage into a second stream consisting predominantly of water and a second stream of reduced water content.

8. The process according to claim 1, wherein the membranes comprise a separation-active layer of polyamide, cellulose acetate or polyether sulphone.

9. The process according to claim 1, wherein the local temperature at the membrane is between 10 and 70° C. and the transmembrane pressure is between 20 and 100 bar.

10. The process according to claim 1, wherein the first stream of reduced water content is wholly or partly returned into the reaction space.

11. The process according to claim 10, wherein the water content and/or catalyst content in the production plant is determined and the additional water and/or catalyst is as necessary fed into the reaction space.

12. The process according to claim 11, wherein the water content and/or catalyst content is determined using an on-line probe or by measuring the water removed by the membrane separation stages.

13. The process according to claim 1, wherein the water content in the inlet to the reaction space is not greater than 75% of the overall mass.

14. The process according to claim 1, wherein at least one stream removed by the membrane separation stages which consists predominantly of water is sent for a biological work-up.

15. The process according to claim 7, wherein the stream which was removed by the second membrane separation stage and consists predominantly of water is sent for a biological work-up.

16. The process according to claim 1, wherein a stream of reduced water content is sent for incineration.

17. The process according to claim 1, wherein the second stream of reduced water content is sent either for incineration and/or to the first membrane separation stage and/or to the reaction space.

18. The process according to claim 1, wherein the first stream of reduced water content is directed either back into the reaction space and/or into an incineration.

19. The process according to claim 1, wherein the aqueous effluent from the bottom part of the distillation column is directed either to the first membrane separation stage and/or back into the reaction space.

* * * * *